(12) United States Patent
Yagyu et al.

(10) Patent No.: US 8,228,493 B2
(45) Date of Patent: Jul. 24, 2012

(54) CARRYING DEVICE AND APPEARANCE INSPECTION DEVICE FOR TEST OBJECTS

(75) Inventors: Motohiro Yagyu, Yamatokoriyama (JP);
Kenichi Kasai, Yamatokoriyama (JP);
Ken Sato, Yamatokoriyama (JP);
Junsuke Yasui, Yamatokoriyama (JP);
Akira Nagao, Yamatokoriyama (JP);
Tetsuhisa Ishida, Yamatokoriyama (JP)

(73) Assignee: Qualicaps Co., Ltd., Nara (JP)

( * ) Notice: Subject to any disclaimer, the term of this patent is extended or adjusted under 35 U.S.C. 154(b) by 313 days.

(21) Appl. No.: 12/602,259

(22) PCT Filed: Apr. 25, 2008

(86) PCT No.: PCT/JP2008/058119
§ 371 (c)(1),
(2), (4) Date: Nov. 30, 2009

(87) PCT Pub. No.: WO2008/155949
PCT Pub. Date: Dec. 24, 2008

(65) Prior Publication Data
US 2010/0214560 A1   Aug. 26, 2010

(30) Foreign Application Priority Data
Jun. 19, 2007   (JP) .................... 2007-161623

(51) Int. Cl.
*G01N 21/00*   (2006.01)
(52) U.S. Cl. ............... 356/237.1; 356/237.2; 356/237.6
(58) Field of Classification Search ..... 356/237.1–237.5
See application file for complete search history.

(56) References Cited

U.S. PATENT DOCUMENTS

| | | | |
|---|---|---|---|
| 5,085,510 A * | 2/1992 | Mitchell | 356/237.1 |
| 6,260,688 B1 | 7/2001 | Steeber et al. | |
| 6,542,235 B1 * | 4/2003 | Caskey et al. | 356/394 |
| 7,701,568 B2 * | 4/2010 | Ackley et al. | 356/237.1 |
| 2004/0130709 A1 * | 7/2004 | Yamamoto | 356/237.1 |
| 2006/0268264 A1 * | 11/2006 | Ackley et al. | 356/237.1 |

FOREIGN PATENT DOCUMENTS

| | | |
|---|---|---|
| JP | 6-80244 | 3/1994 |
| JP | 9-21755 | 1/1997 |
| JP | 9-288061 | 11/1997 |
| JP | 11-301601 | 11/1999 |
| JP | 11-304721 | 11/1999 |
| JP | 2000-161916 | 6/2000 |
| JP | 2000-292358 | 10/2000 |
| JP | 2001-95898 | 4/2001 |
| JP | 2002-535217 | 10/2002 |
| JP | 2003-155113 | 5/2003 |
| JP | 2005-263467 | 9/2005 |
| JP | 2006-53033 | 2/2006 |
| WO | 00/43294 | 7/2000 |

OTHER PUBLICATIONS

Japanese Office Action (along with English translation) issued Dec. 7, 2007 in Application No. 2007-161623.
Japanese Office Action (along with English translation) issued Apr. 30, 2008 in Application No. 2007-161623.
International Search Report issued Jul. 8, 2008 in International (PCT) Application No. PCT/JP2008/058119.

* cited by examiner

*Primary Examiner* — Tarifur Chowdhury
*Assistant Examiner* — Isiaka Akanbi
(74) *Attorney, Agent, or Firm* — Wenderoth, Lind & Ponack, L.L.P.

(57) ABSTRACT

A test object carrying device for use in an appearance inspection device for checking the appearance of the test objects, which includes a back/front reversal unit for turning over the test objects being conveyed by the forward conveying means and supplying them to the returning unit; the back/front reversal means is provided with a first drum for rotating and conveying the test objects unit while holding the test objects on the peripheral surface thereof, and a second drum for rotating and conveying the test objects being conveyed by the first drum while holding the test objects on the peripheral surface thereof; wherein at least one of the first drum and the second drum is structured so that the test objects are transferred in parallel to the forward conveying unit and returning unit by rotating and conveying the test objects while holding them on the peripheral surface thereof.

6 Claims, 12 Drawing Sheets

CARRYING DEVICE AND APPEARANCE INSPECTION DEVICE FOR TEST OBJECTS

BACKGROUND OF THE INVENTION

I. Technical Field

The present invention relates to a carrying device for conveying tablets, capsules or like test objects, and an appearance inspection device for inspecting the appearance of the test objects conveyed by the carrying device.

II. Description of the Related Art

There are several conventionally known devices that inspect the appearance of tablets or like test objects while conveying them, so that defects, such as the adhesion of foreign matter, contamination, and cracking on/in the test objects, can be detected. For example, Japanese Unexamined Patent Publication No. 1997-21755 discloses an appearance inspection device by which all of the surfaces of the test objects can be inspected by conveying them while rotating them with a plurality of rollers and taking several images of the rotating test objects from an upper oblique direction.

SUMMARY OF THE INVENTION

However, because the inspection device disclosed in Japanese Unexamined Patent Publication No. 1997-21755 rotates the test object using friction between the object and the rollers, depending on the shape, the surface roughness, etc., of the test object, there is a risk that images may be captured while the test object is not smoothly rotating. This causes partial images of the test object to be captured, hindering an accurate appearance inspection.

An object of the present invention is to provide a carrying device that carries test objects in such a manner that the entire appearance of the objects can be easily and reliably inspected. Another object of the present invention is to provide an appearance inspection device provided with such a carrying device.

An object of the present invention can be achieved by a test object carrying device for use in inspecting the appearance of test objects, which is provided with a forward conveying means for conveying the test objects in a forward direction; a returning means for conveying the test objects in the direction opposite to that of the forward conveying means, the returning means being disposed in parallel to the forward conveying means; and a back/front reversal means for turning over the front and back surfaces of the test objects being conveyed by the forward conveying means and supplying the test objects to the returning means.

The back/front reversal means is provided with a first drum for rotating and conveying the test objects being conveyed by the forward conveying means while holding the test objects on the peripheral surface thereof; and a second drum for rotating and conveying the test objects being conveyed by the first drum while holding the test objects on the peripheral surface thereof.

At least one of the first drum and the second drum is structured so that the test objects are shifted in parallel to the forward conveying means and returning means by rotating and conveying the test objects while holding them on the peripheral surface thereof.

Another object of the present invention can be achieved by an appearance inspection device having the carrying device for conveying test objects as described above. The appearance inspection device is provided with a plurality of image-pickup means for capturing the images of each test object from upper oblique directions along the same scanning line while the test objects are being conveyed by the forward conveying means and returning means. The appearance inspection device is also provided with a defect detection means for detecting any defects based on image data captured by the image-pickup means.

The carrying device for test objects and the appearance inspection device of the present invention makes it possible to convey test objects in such a manner that their entire appearance can be reliably and readily inspected.

DETAILED DESCRIPTION OF THE INVENTION

Figure 1:
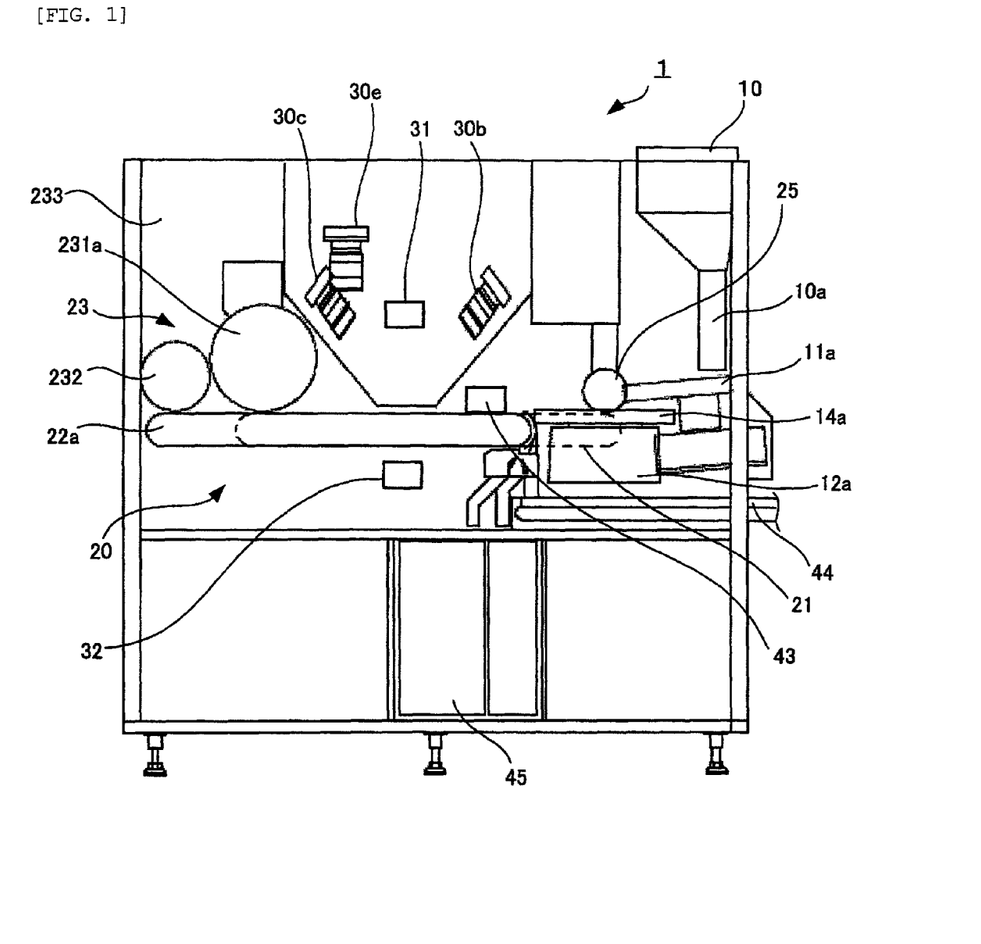
FIG. 1 is a side elevation view of an appearance inspection device according to one embodiment of the present invention.

Hereunder, embodiments of the present invention are explained in detail with reference to the attached drawings. FIG. 1 shows a side elevation view of the appearance inspection device according to one embodiment of the present invention, and FIG. 2 is a plan view of the main components of the appearance inspection device of FIG. 1.

Figure 2:
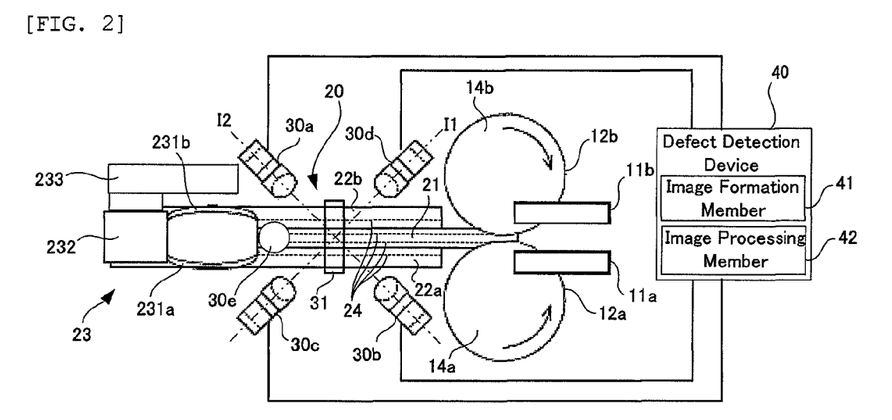
FIG. 2 is a plan view of the main components of the appearance inspection device of FIG. 1.

As shown in FIGS. 1 and 2, the appearance inspection device 1 is provided with a hopper 10 through which tablets or like test objects are supplied; vibrating feeders 12a and 12b for conveying the test objects supplied from the hopper 10 while aligning them; a carrying device 20 for conveying the test objects sequentially supplied from the vibrating feeders 12a and 12b; five image-pickup devices 30a, 30b, 30c, 30d and 30e for capturing images of the test objects being conveyed by the carrying device 20; and a defect detection device 40 for detecting the existence of defects in the test objects based on image data of each of the image-pickup devices 30a to 30e.

The vibrating feeders 12a and 12b are adjacently provided on the right and left of the hopper 10. The test objects are supplied from the two outlets 10a and 10b formed in the lower portion of the hopper 10 to the vibrating feeders 12a and 12b via chutes 11a and 11b respectively. The test objects supplied to the vibrating feeders 12a and 12b are conveyed in the direction shown by the arrow in FIG. 2. A detailed explanation of the conveying mechanism of the vibrating feeders 12a and 12b is omitted here because it is the same as that of known ones using elliptic oscillation.

Figure 3:
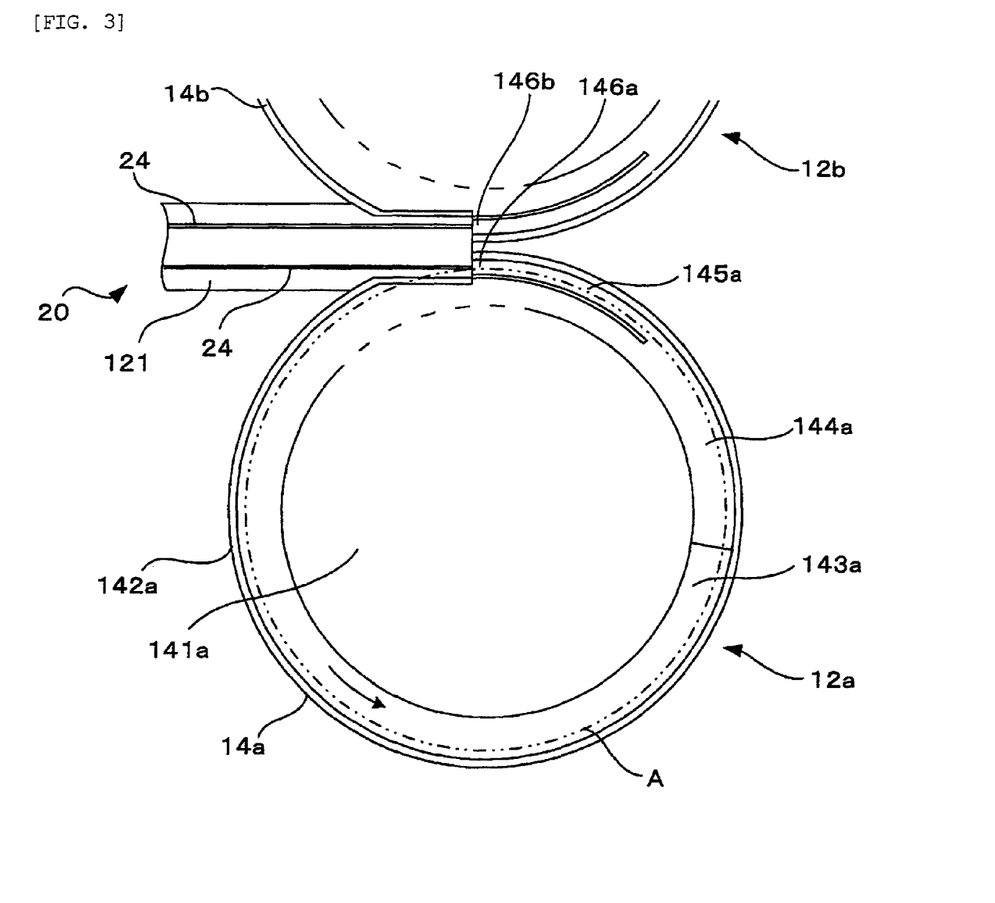
FIG. 3 is an enlarged plan view of the vibrating feeder of FIG. 1.

FIG. 3 shows an enlarged plan view of a feeder ball 14a that serves as a conveyance plane of the vibrating feeder 12a. The feeder ball 14a has a circular bottom wall 141a supported by a vibrating shaft (not shown) of the vibrating feeder 12a, and an annular guide wall 142a provided along the rim of the bottom wall 141a. At the periphery of the bottom wall 141a, an ascending rail 143a, descending rail 144a, and guide rail 145a are disposed in such a manner that they sequentially connect in this order along the guide wall 142a.

Figure 4:
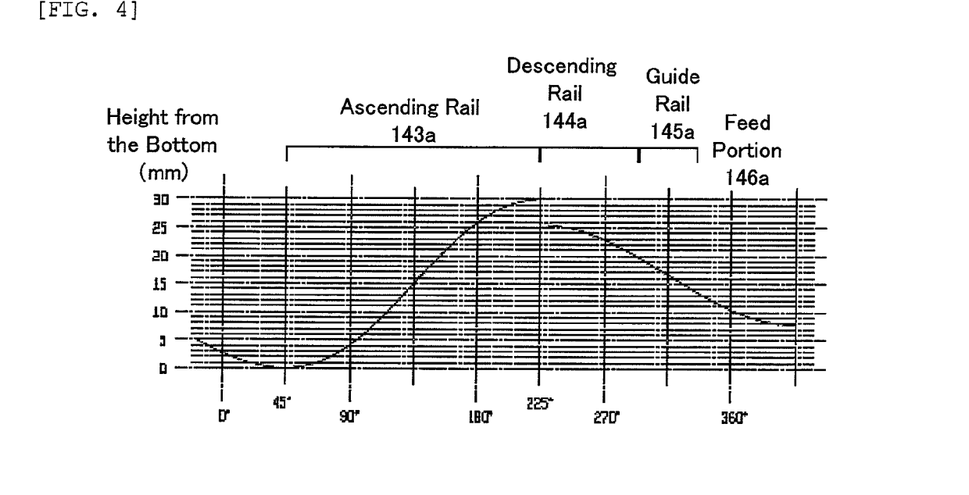
FIG. 4 is a side elevation view of the vibrating feeder of FIG. 3 taken along the chain double-dashed line A.

FIG. 4 shows side views of inclinations of the ascending rail 143a, descending rail 144a and guide rail 145a of FIG. 3 along the chain double-dashed line A. The ascending rail 143a has an ascending inclination along the guide wall 142a. The inclination of the ascending rail changes so as to form a smooth curve, i.e., the inclination is small at the beginning, gradually increases, and then decreases again at the end. The descending rail 144a has a descending inclination along the guide wall 142a whose inclination gradually becomes greater in the conveying direction. The guide rail 145a has a descending inclination continuing from the descending rail 144a and conveys the test objects in a line.

When vibration is applied to the feeder ball 14a, the test objects on the bottom wall 141a ascend in accordance with the inclination of the ascending rail 143a and then descend in accordance with the descending rail 144a. The ascending rail 143a and descending rail 144a incline in the circumferential direction, and they also downwardly incline in the outer radial direction. Therefore, the objects are linearly guided to the guide rail 145a along the guide wall 142a. Excess test objects that are not introduced in the guide rail 145a fall on the bottom wall 141a and are then guided to the ascending rail 143a again by vibration conveyance.

The structure of the vibrating feeder 12b is similar to that of the vibrating feeder 12a described above. Accordingly, test objects are aligned and conveyed from the feed portions 146a and 146b of the vibrating feeders 12a and 12b toward the carrying device 20.

The carrying device 20 is provided with a forward conveying member 21, return conveying members 22a and 22b, and a back/front reversal device 23. The forward conveying member 21 receives the test objects from the vibrating feeders 12a and 12b and conveys them in two lines (right and left). The return conveying members 22a and 22b are disposed on the right and left of the forward conveying member 21 and linearly convey the test objects in the direction opposite to the conveying direction of the forward conveying member 21. The back/front reversal device 23 receives the test objects from each line of the forward conveying member 21, turns over the test objects and then transfers them to the return conveying members 22a and 22b.

Both the forward conveying member 21 and the return conveying members 22a and 22b are formed from conveyor belts, which are driven at the same speed by a servomotor or the like. Each of the conveying belts is formed of a milky-colored semitransparent material with light transmittance and light diffusibility. For example, a polyester belt provided by Nitta Corporation (product name: New Light Grip P-0) is usable. The conveying belt does not have to be milky-colored. It is preferable that the conveying belt be a light color that can exhibit light transmittance and light diffusibility for reliably inspecting the appearance of the test object D as described later. Specifically, the conveying belt has a Munsell value of preferably not less than 7, more preferably not less than 7.5, and particularly preferably not less than 8. However, even when the Munsell value of the conveying belt is about 5, reliable appearance inspection can be conducted if the lightness of the test object itself is low. The conveying belt may be formed of a transparent material, and the same effects as those of the present embodiment can also be achieved in this case. When a conveying belt formed of a transparent material is used, it is preferable that a bright light source be used as a lower lighting device 32.

In the conveyance plane of each conveying belt, a groove 24 extending in the conveying direction is formed so as to correspond to each line of the conveyed test objects. The groove has a circular cross section (including an elliptic arc) having a width smaller than that of the test object, and a depth that can hold only a portion of the test object (for example, in the case of tablets, about 0 to 1 mm). Press rollers 25 are provided at the location where the test objects are transferred from the vibrating feeder 12a (12b) to the forward conveying member 21, as shown in FIG. 1.

Figure 5:
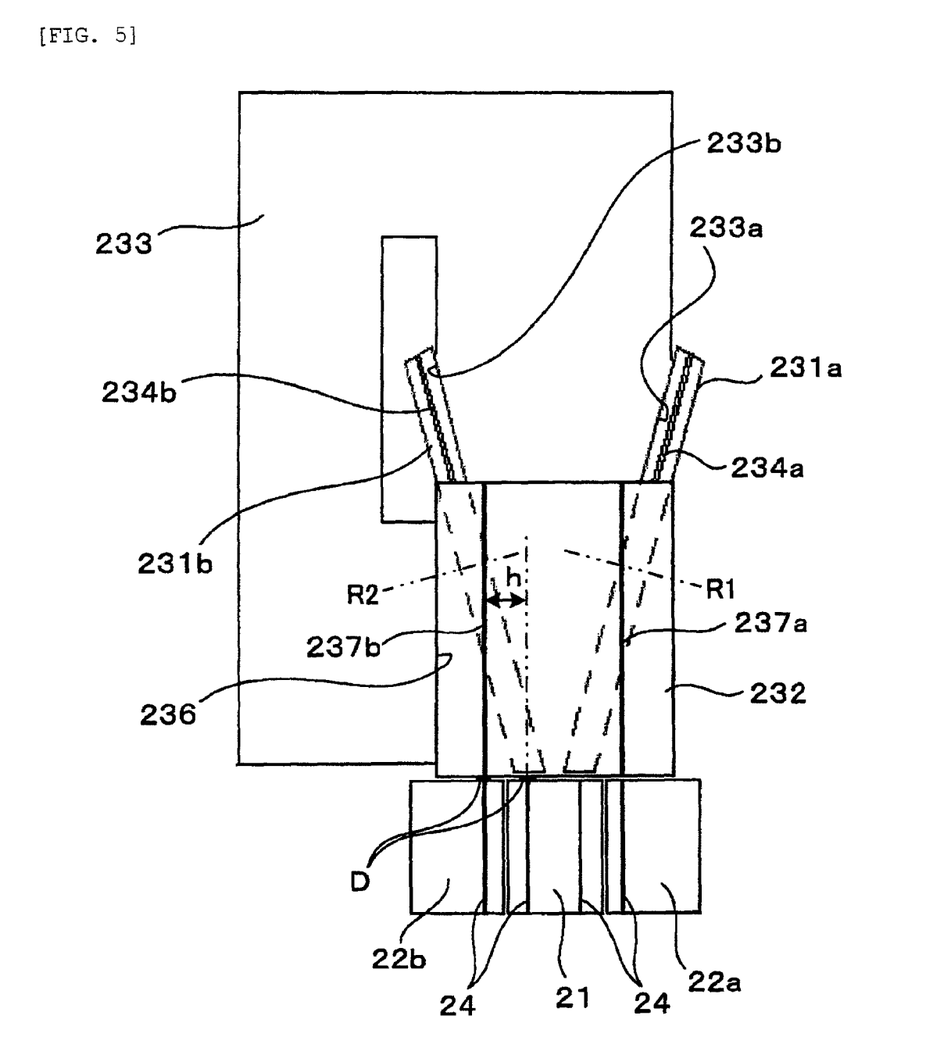
FIG. 5 shows the rear surface of the back/front reversal device of FIG. 1.
Figure 6:
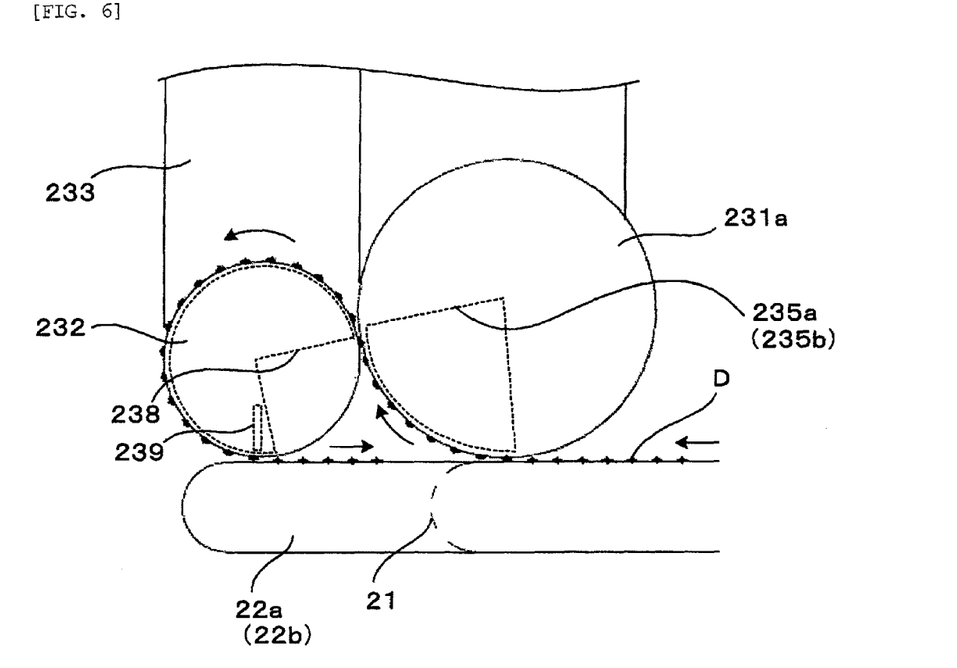
FIG. 6 is an enlarged side view of the back/front reversal device of FIG. 1.

As shown in FIGS. 5 and 6, the back/front reversal device 23 is provided with inclined drums 231a and 231b and an inversion drum 232. The inclined drums 231a and 231b are slidably and rotatably supported relative to the inclined surfaces 233a and 233b, which are disposed on the right and left sides of the suction box 233 that is connected to a vacuum pump (not shown). In this structure, as shown in FIG. 5, when seen along the conveying direction of the forward conveying member 21 and return conveying members 22a and 22b, the rotation axes R1 and R2 are arranged so as to be inclined relative to the conveyance planes of the forward conveying member 21 and return conveying members 22a and 22b (i.e., when the appearance inspection device 1 is placed on a horizontal floor, they are inclined relative to the horizontal surface).

The shapes of the inclined drums 231a and 231b and inversion drum 232 may be disc-like, rather than the usual cylinder-like (drum) shape. In the present embodiment, the inclined drums 231a and 231b have a disc-like shape and the inversion drum 232 has a cylinder-like shape.

In the peripheral surfaces of the inclined drum 231a and 231b, many suction ports 234a and 234b are continuously formed along the circumferential direction. The suction ports 234a and 234b are communicably opened to the inside of the suction box 233 via the notches 235a and 235b in the inclined surfaces 233a and 233b of the suction box 233. This arrangement allows the inclined drums 231a and 231b to hold, by means of suction, each of the test objects D conveyed in each line of the forward conveying member 21, and then to transfer them in the direction shown by the arrow in FIG. 6.

The inversion drum 232 is supported in such a manner that its rotation axis extends in the horizontal direction so that the inversion drum 232 rotates by sliding relative to the perpendicular plane 236 of the suction box 233. In both sides of the peripheral surfaces of the inversion drum 232, many suction ports 237a and 237b are continuously formed along the circumferential direction. The suction ports 237a and 237b are communicably opened to the inside of the suction box 233 via the notch 238 formed in the perpendicular plane 236. This arrangement allows the test objects D conveyed by the inclined drum 231a and 231b to rotate with inclination and be transferred to the suction ports 237a and 237b of the inversion drum 232 at a location separated therefrom by the distance h in parallel to the direction in which the forward conveying member 21 and the return conveying members 22a and 22b are arranged (i.e., perpendicular to the conveying direction along the conveyance plane), and then the test objects D are held by suction on the peripheral surface of the inversion drum 232.

The transfer distance h of the test objects D in the parallel direction corresponds to the distance between the groove 24 of the forward conveying member 21 and the groove 24 of the return conveying members 22a and 22b. The test objects D are guided above the grooves 24 of the return conveying members 22a and 22b by the rotation of the inversion drum 232 in the direction shown by the arrow of FIG. 6, and then transferred to the return conveying members 22a and 22b by injecting compressed air from the compressed air nozzle 239.

As shown in FIGS. 1 and 2, five image-pickup devices 30a, 30b, 30c, 30d, and 30e are disposed in the vicinity of the forward conveying member 21 and the return conveying members 22a and 22b in such a manner that images of the test objects D being conveyed can be captured from upper directions. Lighting devices 31 and 32 are disposed immediately above and below the forward conveying member 21 and the return conveying members 22a and 22b. The lighting devices 31 and 32 illuminate the test objects D by guiding the light emitted from an incandescent lamp or like light source using optical fiber.

All of the image-pickup devices 30a to 30e are line sensor cameras, which scan in the direction intersecting the image-pickup axis and output the signals corresponding to the lightness of the test objects D (i.e., output the signals substantially proportional to the light amount received by the line sensors). Among the image-pickup devices 30a to 30e, two image-pickup devices 30a and 30b are arranged so that they face each other on the image-pickup axis 11 as seen in a plan view. Two other image-pickup devices 30c and 30d are arranged so that they face each other on image-pickup axis 12 that perpendicularly intersects the image-pickup axis 11 as seen in a plan view. The image-pickup devices 30a to 30d are arranged so that they can substantially simultaneously capture images of the test objects D being conveyed in two lines by the forward conveying member 21, and, the test objects D being conveyed by return conveying members 22a and 22b in one line from upper oblique directions on the image-pickup axis I1 or I2. In other words, each image-pickup device 30a to 30d can simultaneously capture an image of four test objects D in each conveying line along the same scanning line.

The remaining image-pickup device 30e is disposed so as to capture images of the test objects D from directly above. In other words, the image-pickup device 30e can capture images of the front surfaces of the test objects D being conveyed by the forward conveying member 21 and the back surfaces of the test objects D being conveyed by the return conveying members 22a and 22b along the same scanning line.

The defect detection device 40 is provided with an image formation member 41 and an image processing member 42. The image formation member 41 generates two-dimensional image data of the test objects D based on the output signals from each of the image-pickup devices 30a to 30e. The image processing member 42 extracts the region in which the amount of light received is less than a predetermined level from the image data generated by the image formation member 41 to conduct inspection. The defect detection device 40 determines whether or not the individual test object D passes or fails the inspection based on the inspection results of the image processing member 42. Each of the test objects D conveyed by the return conveying members 22a and 22b is classified into "accepted" or "rejected" using the screening device 43. The accepted test objects D are transferred onto a defect-free product recovery belt 44 to be picked up. The rejected objects are discharged into a defective product holder 45.

The operation of the appearance inspection device 1 is explained below. In FIGS. 1 and 2, when many objects to be tested, such as tablets, are placed in the hopper 10, the objects are supplied to the vibrating feeders 12a and 12b via the chutes 11a and 11b, and then conveyed along the ascending rail 143a, descending rail 144a, and guide rail 145a shown in FIG. 3.

Figure 7:
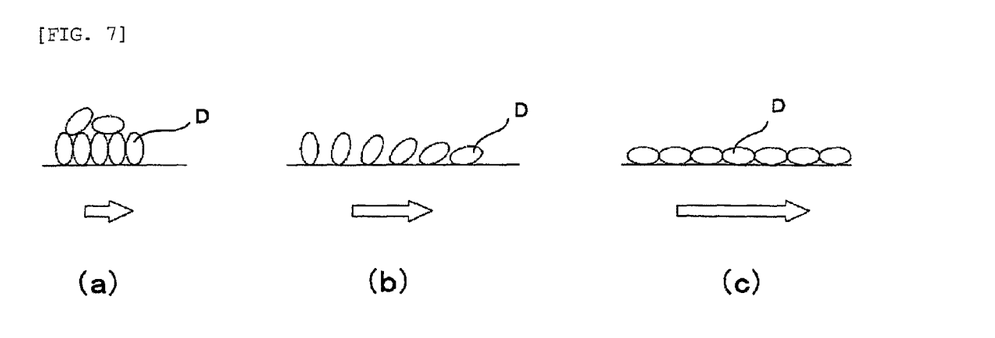
FIG. 7 is a drawing that illustrates the conditions for conveying the test object by the vibrating feeder of FIG. 1.
Figure 8:
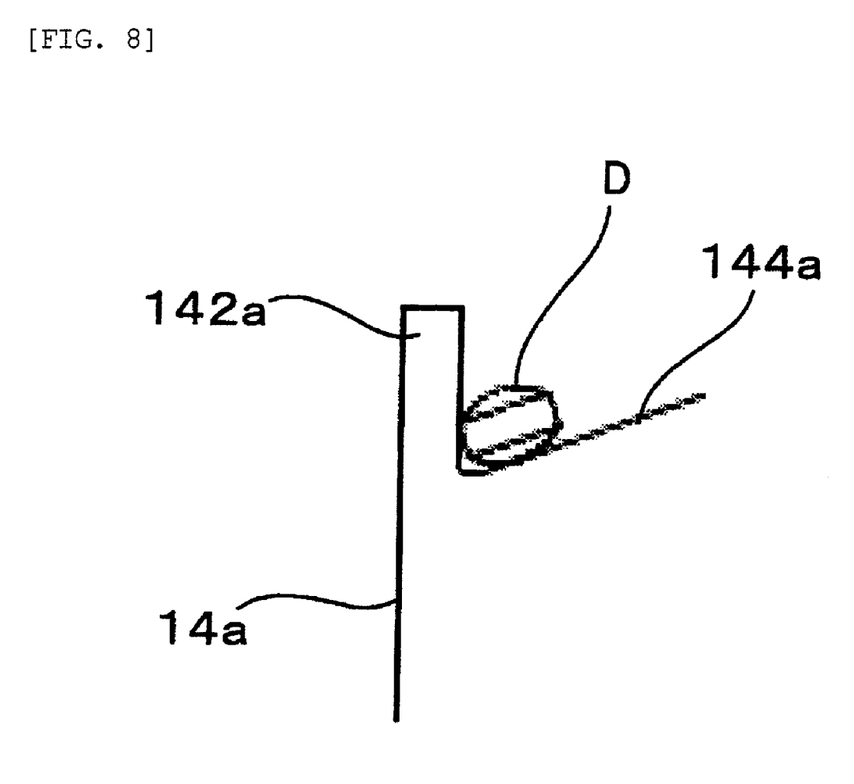
FIG. 8 is a cross-sectional view that illustrates the conditions for conveying the test object by the vibrating feeder of FIG. 1.

Each of the ascending rail 143a, descending rail 144a, and guide rail 145a has an inclination as shown in FIG. 4. Therefore, the test objects are conveyed at a low speed on the ascending rail 143a, which has an acclivity, and they are conveyed at a higher speed on the descending rail 144a, which has a declivity. Accordingly, the aggregation of the test objects D conveyed on the ascending rail 143a as shown in FIG. 7(a) breaks into individual pieces as shown in FIG. 7(b) when they are transferred onto the descending rail 144a and their speed is accelerated. Therefore, while being conveyed on the descending rail 144a, the test objects D are aligned as shown in FIG. 7(c). As shown in FIG. 8, the descending rail 144a allows the test objects D to align along the guide wall 142a before being supplied to the guide rail 145a, so that the test objects D can be introduced into the guide rail 145a smoothly. The guide rail 145a is structured so that the test objects pass through in a single line.

As described above, by providing the vibrating feeder with a descending rail lying between the ascending rail and the guide rail, it becomes easier to suitably differentiate the conveying speed of the test objects. This facilitates the conveyance of the test objects in an aligned state regardless of their shape. In other words, this arrangement allows the test objects to be automatically aligned using their own weight, and therefore eliminates the need for a regulation plate for forcibly aligning the objects. Even if a regulation plate is provided, collisions of the test objects and the regulation plate can be prevented and the risk of chipping or cracking of the test objects can be reduced. The greater the difference in the speed between the ascending rail and the descending rail, the more remarkable the effects. Therefore, the vibrating feeder of the present invention is particularly effective when high-speed conveyance is performed (for example, 100,000 to 160,000 tablets an hour per line).

The inclination angle and connection location of the ascending rail and the descending rail can be suitably selected depending on the conveyance amount and shape of the test objects so that the test objects can be easily aligned. For example, as in the present embodiment, by making the inclination angle of the descending rail gradually increase in the conveying direction, test objects being conveyed in bulk can be gradually spread apart. Accordingly, the conveyance speed can be made greatest immediately before entering the guide rail so that alignment of the test objects becomes easier.

In addition to adjusting the inclination angles of the ascending rail and the descending rail, it is also possible to incline the entire conveyance plane relative to the horizontal surface by providing the vibrating feeder on a slope. This ensures a more stable distribution of conveyance speed. Even if a vibrating feeder is provided with only an ascending rail on a bottom wall having a flat surface, by disposing the vibrating feeder in an inclined state, downward inclination can be obtained. Therefore, a desirable difference in conveyance speed can be generated between the test objects being conveyed on the ascending rail and those on the flat surface by applying a positive acceleration to the test objects, achieving the same effects as those of the present embodiment. Furthermore, even if a vibrating feeder has only a bottom wall with a flat surface and no ascending rail and descending rail are provided, by arranging this vibrating feeder in an inclined state, portions that each serve as an ascending rail and a descending rail can be provided on both sides of the bottommost surface of the flat surface. This also achieves the same effects as those of the present embodiment.

Figure 9:
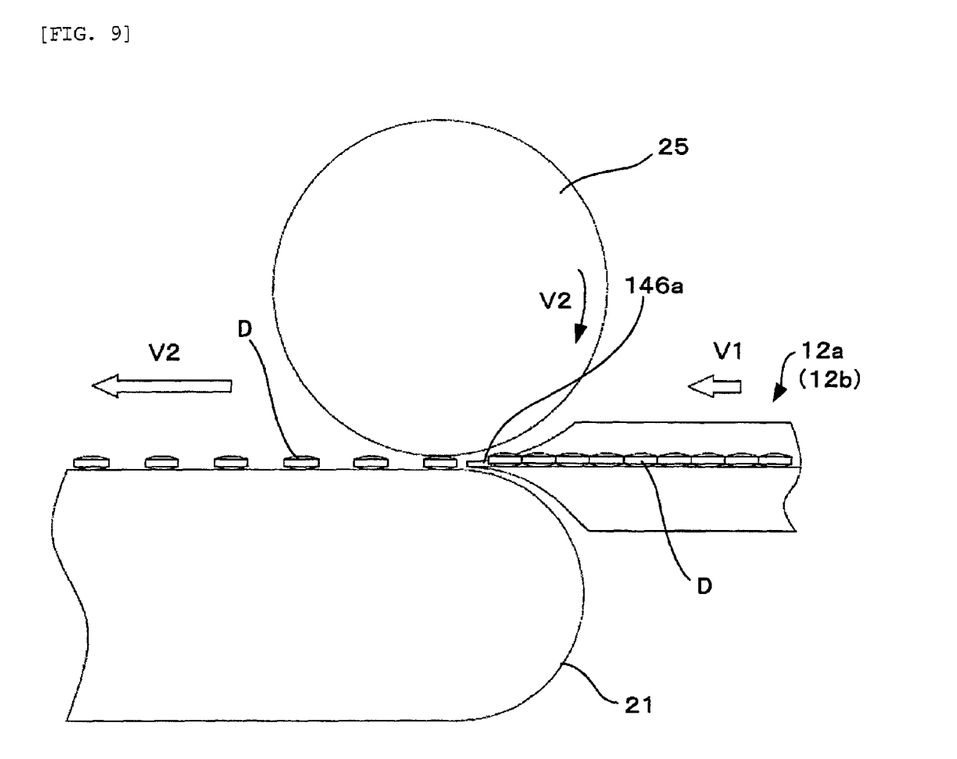
FIG. 9 is an enlarged side view showing the area around the press rollers 25 of FIG. 1.

The aligned test objects discharged from the feed portions 146a and 146b of the vibrating feeders 12a and 12b are transferred onto the forward conveying member 21. As shown in FIG. 9, by setting the supply speed from the vibrating feeders 12a and 12b as V1, and the conveyance speed of the forward conveying member 21 as V2, which is faster than V1, the space between the test objects D in each line of the forward conveying member 21 can be widened. A desirable space can be obtained by adjusting the difference between V1 and V2. The press rollers 25 rotate at substantially the same speed as the conveyance speed V2 of the forward conveying member 21. This prevents jumping or misalignment of the test objects D when transferred from the vibrating feeders 12a and 12b to the forward conveying member 21, and reliably positions the test objects D on the groove 24 of the forward conveying member 21.

Figure 10:
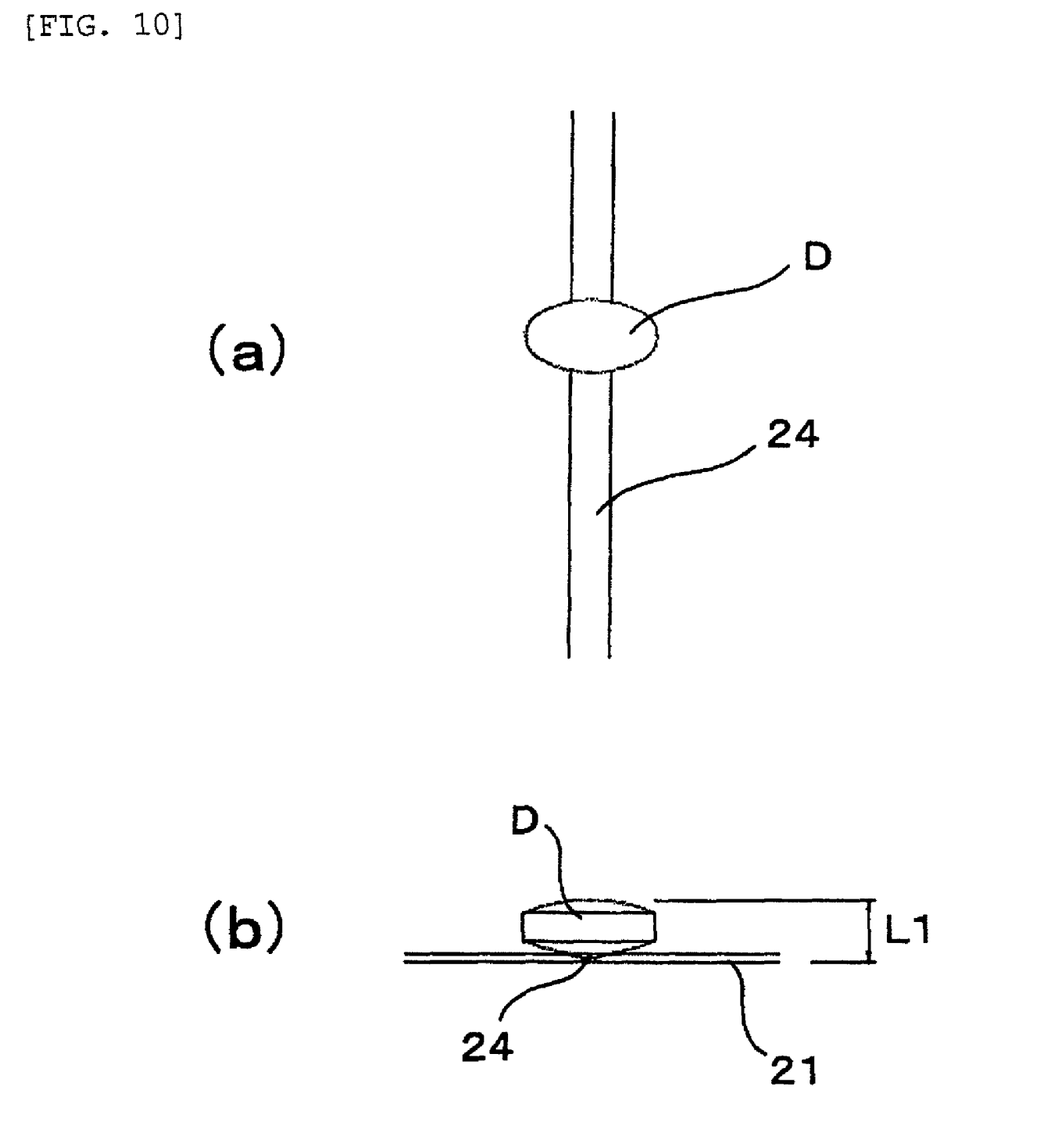
FIG. 10 is a view that illustrates the conditions for conveying the test object by the forward conveying member of FIG. 1.
Figure 11:
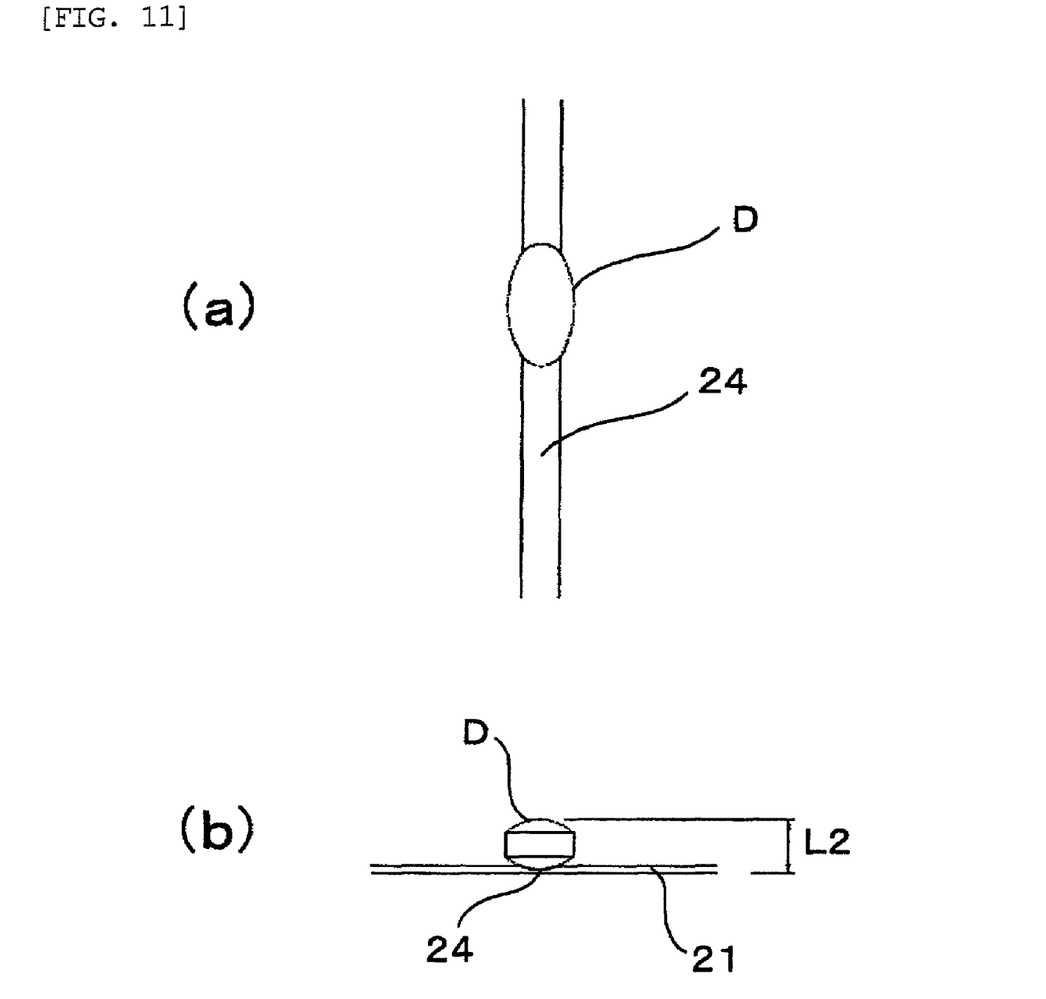
FIG. 11 is a view that illustrates the conditions for conveying the test object by the forward conveying member of FIG. 1.

As shown in FIG. 10(a), part of the bottom surface of each test object D positioned on the groove 24 is placed in the groove 24. Therefore, as shown in FIG. 10(b), the height L1 of the forward conveying member 21 as measured from the conveyance plane becomes slightly shorter than the actual height of the object. When the test objects D horizontally rotate while being conveyed on the forward conveying member 21, the test objects D are stabilized in the position (direction) that makes the height from the conveyance plane of the forward conveying member 21 shorter, as shown in FIGS. 11(a) and 11(b), and conveyed while maintaining the position in which the height becomes the lowest L2

By forming grooves 24 in the forward conveying member 21, even if the test objects are irregularly shaped tablets or capsules, they can automatically be adjusted so that their position is most stable. This arrangement allows each test object to be conveyed in an aligned condition with a fixed position. It is preferable that the groove 24 have a circular (including an elliptic arc) cross section as in the present embodiment. This arrangement allows the test objects to easily change their height from the conveyance plane in accordance with their position. However, the cross section of the groove 24 does not have to be an arc and may be rectangular. If the test objects D have a cross section that does not cause a change in the position during the conveyance, such as a square shape, the groove 24 may be omitted.

The test objects D, after having their positions adjusted on the forward conveying member 21, pass through the image-pickup area where image-pickup devices 30a to 30e are provided. Subsequently, they are turned over by the back/front reversal device 23, and then conveyed in the opposite direction by the return conveying members 22a and 22b. The operation of the back/front reversal device 23 is the same as that explained above, i.e., by passing through the inclined drum 231a and 231b and the inversion drum 232, which can hold the test objects on the peripheral surfaces thereof, the test objects transferred to the return conveying members 22a and 22b can be reliably turned over. By placing the test objects D in the groove 24 of the return conveying members 22a and 22b, the positions of the test objects D conveyed by the return conveying members 22a and 22b can also be automatically adjusted. The conveyance of the test objects D in the forward direction by the forward conveying member 21 and in the reverse direction by the return conveying members 22a and 22b can thus be continuously conducted.

In the image-pickup area of each image-pickup device 30a to 30e, the test objects D are irradiated from the top and bottom surfaces thereof with light emitted from the lighting devices 31 and 32. Because the conveying belt used in the forward conveying member 21 and return conveying members 22a and 22b of the present embodiment has a highly light color, i.e., a milky-colored semitransparent belt, with light transmittance and light diffusion, the test objects D can be uniformly illuminated by radiating light from the top and bottom surfaces of the test objects D. This arrangement also makes the light color that serves as the background of the test objects D conspicuous, so the test objects D are observed as dark portions.

Figure 12:
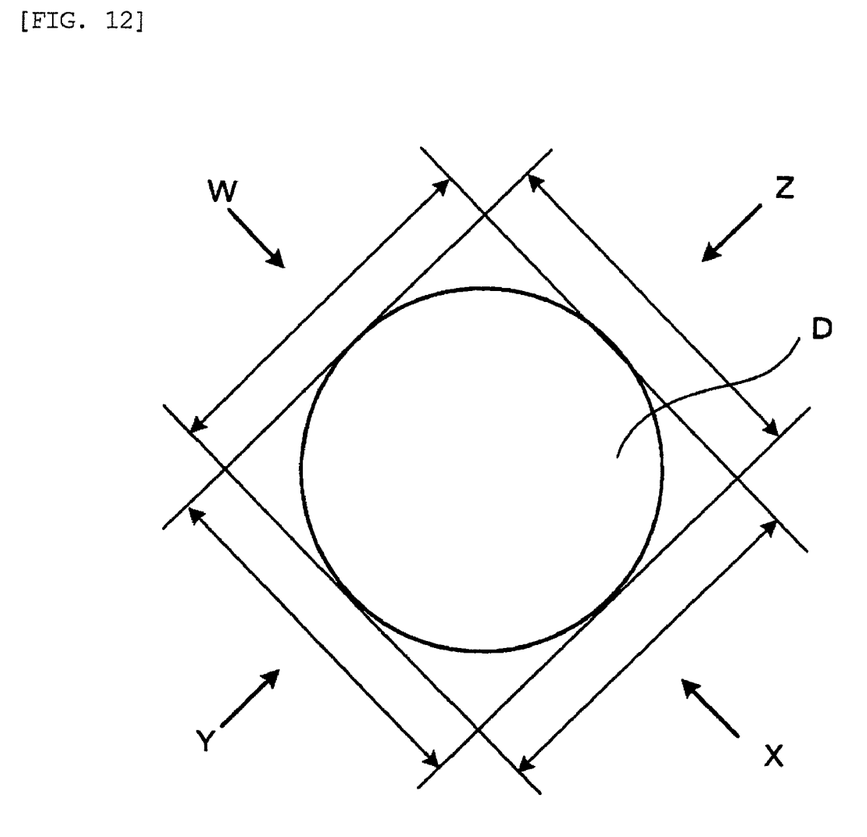
FIG. 12 shows the image-pickup direction as seen in a plan view of the image-pickup device of FIG. 1.

Each of the four image-pickup devices 30a to 30d scans in the direction perpendicular to the image-pickup axis I1, I2 shown in FIG. 2, so that images of individual test objects D being conveyed on the forward conveying member 21 and the return conveying members 22a and 22b can be captured. As a result, images of the top surface of a test object D being conveyed on the forward conveying member 21 are captured from four upper oblique directions W, X, Y, and Z as shown in FIG. 12. Likewise, images of the back surface of a test object D being conveyed on the return conveying members 22a and 22b are captured from four upper oblique directions. Accordingly, a single line of scanning conducted by the image-pickup devices 30a to 30d makes it possible to generate output signals having a degree of light that corresponds with the receptive light. By repeatedly conducting the scanning while conveying the test objects D, the output signals corresponding to the scanning are sequentially transmitted to the defect detection device 40.

In the present embodiment, the forward conveying member 21 and the return conveying members 22a and 22b are disposed in parallel and arranged so that each test object is conveyed in such a manner that its top and back surfaces are exposed. Therefore, by simultaneously taking images of each test object conveyed on the forward conveying member 21 and the return conveying members 22a and 22b along the same scanning line using a plurality of image-pickup devices 30a to 30d, the entire appearance of the test object can be easily and reliably inspected.

In the defect detection device 40, based on the output signals from each of the image-pickup devices 30a to 30d, image formation member 41 generates two-dimensional image data corresponding to the scanning line. For example, when an arbitrary image-pickup device scans a test object D conveyed on the forward conveying member 21 along the scanning line S1 as shown in FIG. 13(a), the image data generated based on the output signals are as shown in FIG. 13(b).

The test objects D are generally tablets, capsules, etc. Therefore, depending on the color of the test objects D, the difference in the lightness of color between the test objects D and the background is very small. This may make it difficult to distinguish the test objects D from background. Because the conveying belt used in the present embodiment is formed of a milky-colored semitransparent material with light transmittance and light diffusion, the lightness on the conveyance plane, which becomes the background, is higher than that of the test objects D. As a result, as shown in FIG. 13(b), in the image data, the portion corresponding to the test object D can be observed as the portion with less lightness (i.e., the amount of light received by the line sensors is small) than the background.

Figure 13:
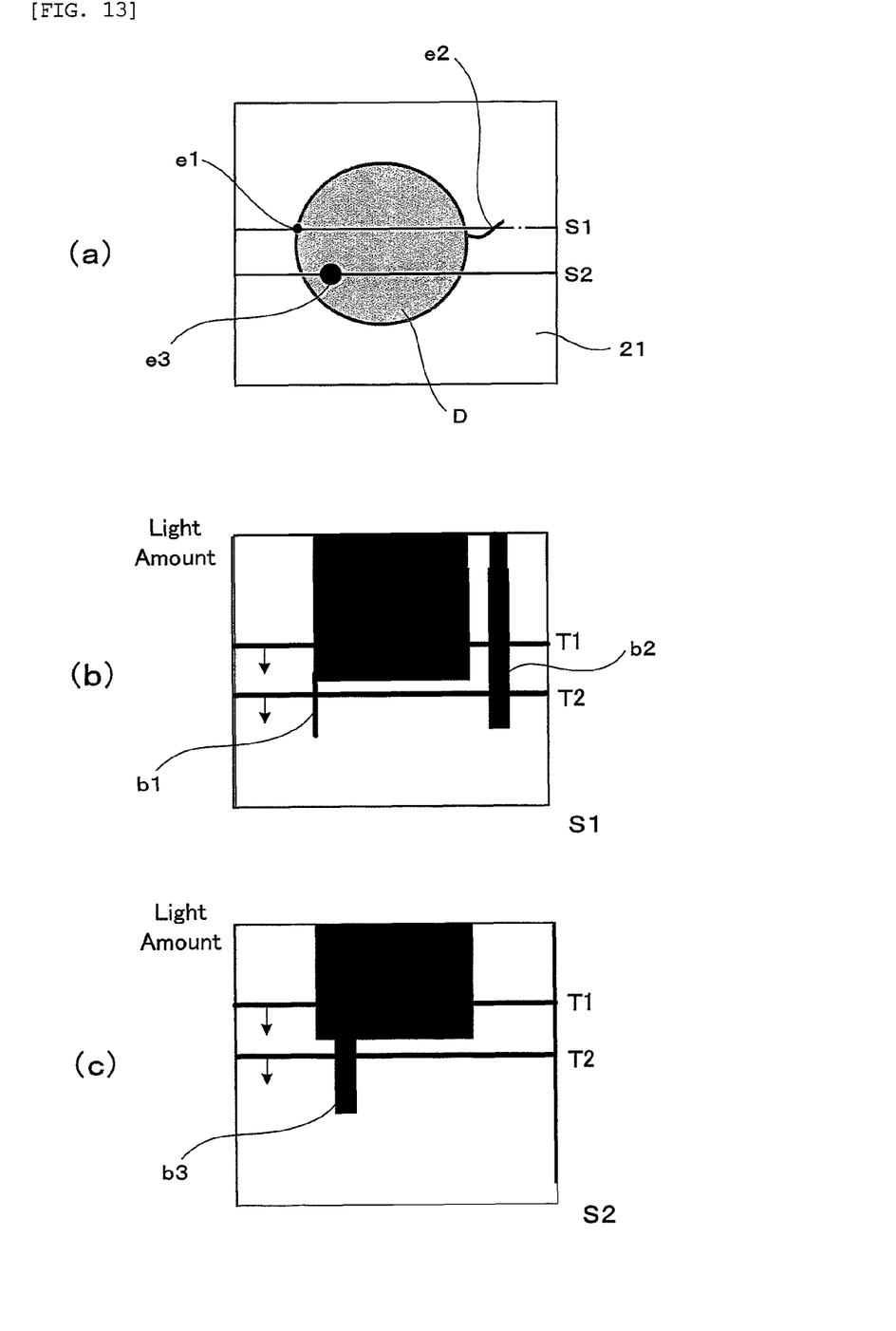
FIG. 13 is a view that illustrates the method for detecting defects based on the image data of the image-pickup device of FIG. 1.

As a result, if a chip e1 and/or a projecting strand of hair e2 exists on the scanning line S1 of the test object D as shown in FIG. 13(a), these defects can be observed as the regions b1 and b2 with less lightness (i.e., the amount of light received by the line sensors is smaller) than that of the test object D as shown in FIG. 13(b). The inspection of test objects D is conducted in the following manner. The first criteria value T1 is set higher than the lightness (the amount of light received by the line sensor) of the test objects D and then the image processing member 42 extracts the image data having a lightness equal to or lower than the first criteria value T1, so that the test objects D can be distinguished from the background. The detection of defects of the test objects D can be conducted by, for example, setting the lightness (the amount of light received by the line sensor) of the second criteria value T2 lower than that of the test objects D, and extracting the image data equal to or lower than the second criteria value T2.

With such a defect detection method, defects protruding from the test object and defects in the edge portions, which are sometimes overlooked by conventional methods because they assimilate with the conveying belt, can be reliably detected. Furthermore, not only the edge portions and the outside of the images of the test object, but also defects that exist inside the test object can be reliably detected. For example, as shown in FIG. 13(a), if a foreign substance is adhered to the test object D on the scanning line S2, the foreign substance can be recognized as the region b3 having a signal value lower than the signal level of the test object D as shown in FIG. 13(c).

In the present embodiment, images of the top and back surfaces of each test object D are captured from four upper oblique directions as described above to detect the presence of defects. This makes it possible to conduct an inspection without a dead angle. In particular, when the test object is annular (doughnut shaped), it is difficult to capture images of the defects on the inside perimeter of the test object by known methods. However, the appearance inspection device of the present embodiment can reliably capture images of such inside perimeters. Combining this with the ability to conduct reliable defect detection of each image data allows the appearance of the test object to be reliably inspected.

In the present embodiment, images of each test object are captured along the same scanning line by each of the image-pickup devices 30a to 30d while the test object is being conveyed on a forward conveying member 21 and the return conveying members 22a and 22b. This makes it possible to inspect the test object by capturing images of the top and back surfaces thereof using the same image-pickup devices 30a to 30d. Therefore, unlike inspections using different image-pickup devices for the front surface inspection and the back side inspection, calibration of the cameras and confirmation of the inspection accuracy do not have to be conducted so often, making camera validation easier.

In the present embodiment, in addition to the above-described four image-pickup devices 30a to 30d, an image-pickup device 30e is further provided for capturing images of the top and back surfaces of the test object in the perpendicular direction. The defect detection device 40 generates image data in the image processing member 42 based on the output signals from the image-pickup device 30e, and detects defects mainly in the printed portion by comparing this image data with the master image.

The forward conveying member 21 and the return conveying members 22a and 22b convey the test objects at a predetermined interval and a predetermined speed. This arrangement allows the defect detection device 40 to specify the test object that corresponds to the image data containing defects by determining the image-pickup device 30a to 30e that captured the signal, based on which the image data are generated in the image formation member 41, and the timing with which the signal is input. When a test object containing a defect is conveyed to the screening device 43, the test object is discharged into the defective product holder 45.

One embodiment of the present invention is explained above, but the embodiments of the present invention are not limited to this. For example, in the present embodiment, the image-pickup devices 30a to 30d face each other on two perpendicularly intersecting image-pickup axes as seen in a plan view, so that the number of image-pickup devices can be reduced while also reliably eliminating a dead angle in the image-pickup. However, as long as no dead angle is formed, various arrangements are possible, and therefore, for example, the image-pickup axes do not have to necessarily intersect at right angles, and the facing arrangement is not necessary.

To simplify camera validation, the present embodiment has a structure in which the forward conveying member 21 and return conveying members 22a and 22b are arranged in parallel, and the image-pickup devices 30a to 30d are disposed so that each of them can capture images of the top and back surfaces of the test object along the same scanning line. However, the image-pickup devices may be arranged so as to capture the images of the test object conveyed by the forward conveying member 21 and the return conveying members 22a and 22b individually. In this case, the forward conveying member 21 and the return conveying members 22a and 22b do not have to be arranged in parallel, and may be arranged differently depending on the installation space.

The number of image-pickup devices for capturing images of a test object from an upper oblique direction is four in the present embodiment; however, as long as a plurality of image-pickup devices are provided, the same effects as those of the present embodiment can be attained. In order to reliably prevent a dead angle, it is preferable that three or more image-pickup devices be provided. It is also preferable that the plurality of image-pickup devices be disposed along the periphery of the image-pickup area with the same interval between each image-pickup device so that uniform images can be captured.

In the carrying device 20 of the present embodiment, one of the return conveying members 22a and 22b is disposed on either side of the forward conveying member 21; however, it is also possible to dispose a forward conveying member on both sides of the return conveying member. Furthermore, the conveyance lines of the forward conveying member 21 and the return conveying members 22a and 22b in the present embodiment consist of two lines, but may be a single line, or three lines or more.

In the present embodiment, the back/front reversal device 23 is provided with the inclined drums 231a and 231b and the inversion drum 232. By positioning the rotation axes of the inclined drums 231a and 231b, which receive test objects from the forward conveying member 21, in such a way that they are inclined relative to the conveyance planes of the forward conveying member 21 and the return conveying members 22a and 22b, the test objects from the forward conveying member 21 to the return conveying members 22a and 22b can be transferred by moving the test objects in a parallel direction relative to which the forward conveying member 21 to the return conveying members 22a and 22b are arranged. The same effect as that of the present embodiment can also be achieved by using an arrangement wherein the drum (first drum) that receives the test objects from the forward conveying member 21 is disposed so that its rotation axis extends along the conveyance planes of the forward conveying member 21 and the return conveying members 22*a* and 22*b* (i.e., along the horizontal surface), and the drum (the second drum), which receives the test objects from the first drum and transfers them to the return conveying members 22*a* and 22*b*, is disposed so that its rotation axis is inclined relative to the conveyance planes. Alternatively, both the above-mentioned first drum and the second drum may be arranged so that their rotation axes are inclined relative to the conveyance planes.

When one or both of the first drum and the second drum are formed as an inclined drum as described above, the inclined drum may be arranged in such a way that its rotation axis is inclined relative to the conveying direction as seen from a position above the conveyance plane. In this case, even if the rotation axis is parallel to the conveyance plane, by rotating and conveying the test objects held on the peripheral surface, the test objects can be transferred in the direction perpendicular to the forward conveying member 21 and the return conveying members 22*a* and 22*b*. This allows the test objects to be transferred from the forward conveying member 21 to the return conveying members 22*a* and 22*b*.

FIG. 1 is a side elevation view of an appearance inspection device according to one embodiment of the present invention.

FIG. 2 is a plan view of the main components of the appearance inspection device of FIG. 1.

FIG. 3 is an enlarged plan view of the vibrating feeder of FIG. 1.

FIG. 4 is a side elevation view of the vibrating feeder of FIG. 3 taken along the chain double-dashed line A.

FIG. 5 shows the rear surface of the back/front reversal device of FIG. 1.

FIG. 6 is an enlarged side view of the back/front reversal device of FIG. 1.

FIG. 7 is a drawing that illustrates the conditions for conveying the test object by the vibrating feeder of FIG. 1.

FIG. 8 is a cross-sectional view that illustrates the conditions for conveying the test object by the vibrating feeder of FIG. 1.

FIG. 9 is an enlarged side view showing the area around the press rollers 25 of FIG. 1.

FIG. 10 is a view that illustrates the conditions for conveying the test object by the forward conveying member of FIG. 1.

FIG. 11 is a view that illustrates the conditions for conveying the test object by the forward conveying member of FIG. 1.

FIG. 12 shows the image-pickup direction as seen in a plan view of the image-pickup device of FIG. 1.

FIG. 13 is a view that illustrates the method for detecting defects based on the image data of the image-pickup device of FIG. 1.

The invention claimed is:

1. A test object carrying device for use in inspecting test object appearance, said device comprising:
 a forward conveying device configured to convey the test objects in a forward direction; and
 a returning device configured to convey the test objects in a direction opposite to the forward direction, the returning device being disposed in parallel to the forward conveying device on left and right sides thereof;
 a back/front reversal device configured to turn over front and back surfaces of the test objects being conveyed by the forward conveying device and to supply the test objects to the returning device;
 the back/front reversal device comprising
 a first drum configured to rotate and convey the test objects being conveyed by the forward conveying device while holding the test objects on a peripheral surface thereof; and
 a second drum configured to rotate and convey the test objects being conveyed by the first drum while holding the test objects on the peripheral surface thereof;
 at least one of the first drum and the second drum being configured so that the test objects are moved in a side-to-side direction while being rotated and conveyed, thereby enabling the second drum to transfer the test objects to the returning device.

2. A test object carrying device according to claim 1, wherein at least one of the first drum and the second drum is disposed in such a manner that the rotation axis thereof is inclined relative to conveyance planes of the forward conveying device and returning device.

3. A test object carrying device according to claim 2, wherein the forward conveying device is configured so as to convey the test objects in first and second lines;
 the returning device is disposed on the left and right sides of the forward conveying device in such a manner that the returning device includes a first and second returning device and the first and second returning devices correspond to the first and second lines of the forward conveying device, respectively;
 the first drum being provided for each line of the forward conveying device and comprising a plurality of inclined drums each of the plurality of inclined drums having a rotation axis that is inclined relative to conveyance planes of the forward conveying device and returning device;
 and the second drum being arranged so as to have a rotation axis extending in a horizontal direction and to be capable of holding the test objects on both peripheral surface edges.

4. A test object carrying device according to claim 1, wherein at least one of the first drum and the second drum is arranged so as to have a rotation axis inclined relative to the conveying direction of the forward conveying device and the returning device.

5. A test object carrying device according to claim 1, wherein each of the forward conveying device and the returning device comprises a conveying belt configured to convey the test objects, and the conveying belt includes a groove extending in the conveying direction.

6. An appearance inspection device provided with the test object carrying device of claim 1, comprising:
 a plurality of image-pickup devices configured to capture images of each test object from upper oblique directions along a same scanning line while the test objects are being conveyed by the forward conveying device and the returning device; and
 a defect detection device configured to detect the presence of defects based on image data captured by the image-pickup devices.

* * * * *